(12) United States Patent
Bajaj et al.

(10) Patent No.: US 11,325,877 B2
(45) Date of Patent: May 10, 2022

(54) PROCESSES FOR THE PRODUCTION OF ETHYLENE OXIDE AND ETHYLENE GLYCOL

(71) Applicant: SHELL OIL COMPANY, Houston, TX (US)

(72) Inventors: Ram Paul Bajaj, Bangalore (IN); Peter Molenaar, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 16/765,647

(22) PCT Filed: Nov. 20, 2018

(86) PCT No.: PCT/EP2018/081844
§ 371 (c)(1),
(2) Date: May 20, 2020

(87) PCT Pub. No.: WO2019/101707
PCT Pub. Date: May 31, 2019

(65) Prior Publication Data
US 2020/0299215 A1  Sep. 24, 2020

(30) Foreign Application Priority Data
Nov. 23, 2017  (EP) .................................... 17203352

(51) Int. Cl.
*C07C 29/74* (2006.01)
*C07C 29/80* (2006.01)
(Continued)

(52) U.S. Cl.
CPC ............. *C07C 29/78* (2013.01); *C07C 29/74* (2013.01); *C07C 29/76* (2013.01); *C07C 29/80* (2013.01); *C07C 31/202* (2013.01)

(58) Field of Classification Search
CPC ................................. C07C 29/76; C07C 29/78
See application file for complete search history.

(56) References Cited

U.S. PATENT DOCUMENTS

| 3,875,019 A | * | 4/1975 | Cocuzza | ................. C07C 29/80 203/18 |
| 4,822,926 A | * | 4/1989 | Dye | ........................ C07C 29/80 568/613 |

(Continued)

FOREIGN PATENT DOCUMENTS

| CN | 100334052 C | * | 8/2007 |
| JP | 04330903 A | * | 11/1992 |
| WO | 20060120207 A1 | | 11/2006 |

OTHER PUBLICATIONS

JPH04330903A, English translation, Nov. 18, 1992, pp. 1-9 (Year: 1992).*

(Continued)

*Primary Examiner* — Medhanit W Bahta
(74) *Attorney, Agent, or Firm* — Shell USA, Inc.

(57) ABSTRACT

A process for the recovery of ethylene glycol from an aqueous stream comprising ethylene glycol is disclosed. The process comprises (a) subjecting an aqueous stream 5 comprising ethylene glycol to an evaporation step in a multiple-effect evaporator to obtain a concentrated stream comprising ethylene glycol; (b) subjecting said concentrated stream comprising ethylene glycol to a first dehydration step in a first dehydrator 10 operating at an overhead pressure in the range of 0 barg (bar gauge) to 4 barg (bar gauge) to obtain a partially dehydrated ethylene glycol stream, and (c) subjecting said partially dehydrated ethylene glycol stream to a second dehydration step in a second dehydrator operating under 15 vacuum to obtain a dehydrated ethylene glycol stream.

12 Claims, 3 Drawing Sheets

(51) Int. Cl.
  *C07C 29/76*   (2006.01)
  *C07C 29/78*   (2006.01)
  *C07C 31/20*   (2006.01)

(56)  References Cited

U.S. PATENT DOCUMENTS

| | | | |
|---|---|---|---|
| 6,417,411 B2 * | 7/2002 | Kakimoto | C07C 29/106 |
| | | | 549/534 |
| 7,825,285 B2 | 11/2010 | Bastings et al. | |
| 8,409,333 B2 | 4/2013 | Beekman et al. | |
| 2002/0010378 A1 * | 1/2002 | Kakimoto | C07D 301/10 |
| | | | 568/867 |

OTHER PUBLICATIONS

CN100334052C, English translation, Aug. 29, 2007, pp. 1-21 (Year: 2007).*

International Search Report and Written Opinion received for PCT Patent Application No. PCT/EP2018/081844, dated Jan. 22, 2019, 08 pages.

* cited by examiner

PROCESSES FOR THE PRODUCTION OF ETHYLENE OXIDE AND ETHYLENE GLYCOL

CROSS REFERENCE TO RELATED APPLICATIONS

This is a national stage application of International application No. PCT/EP2018/081844, filed 20 Nov. 2018, which claims priority of European application No. 17203352.4, filed 23 Nov. 2017.

FIELD OF THE INVENTION

The present invention relates to a process for the recovery of ethylene glycol, most suitably within an integrated ethylene oxide/ethylene glycols process.

BACKGROUND OF THE INVENTION

Ethylene oxide (EO) is used as a chemical intermediate, primarily for the production of ethylene glycols but also for the production of ethoxylates, ethanol-amines, solvents and glycol ethers. It is produced by the direct oxidation of ethylene with oxygen or air. Ethylene and oxygen are passed over a silver oxide catalyst, typically at pressures of 10-30 bar and temperatures of 200-300° C. The reaction is exothermic and a typical reactor consists of large bundles of several thousand tubes that are packed with catalyst. A coolant surrounds the reactor tubes, removing the reaction heat and permitting temperature control.

The product stream from the ethylene oxide reactor is supplied to an ethylene oxide absorber. The absorber has an initial quench section wherein the product stream is contacted with a cooled, recirculating aqueous quench stream and a basic solution is continuously added to the recirculating quench stream. The gas stream passes from the quench section to the main section of the ethylene oxide absorber where it is scrubbed with water to recover ethylene oxide.

The resulting water stream, which is rich in ethylene oxide, is referred to as the fat absorbent and is sent to an ethylene oxide stripper. In the ethylene oxide stripper, the ethylene oxide is stripped from the fat absorbent and a concentrated ethylene oxide stream is sent to ethylene oxide finishing processes such as condensation, distillation and re-absorption. The remaining liquids, referred to as the lean absorbent, are recycled to the ethylene oxide absorber. A residual ethylene oxide absorber is used to recover uncondensed ethylene oxide from the light ends left after condensing ethylene oxide/water vapor from the ethylene oxide stripper overhead.

The residual gases that remain after recovery of the bulk ethylene oxide product are recycled to the ethylene oxidation reactor. Customarily, a small bleed stream is withdrawn from the recycled gases to prevent build-up of impurities such as argon, ethane or nitrogen in the recycle gas loop. A side stream, being part or all of the recycle gas, is usually scrubbed with an aqueous carbon dioxide ($CO_2$) absorbent for removal of excess $CO_2$ which is subsequently stripped from the absorbent in a $CO_2$ stripper and typically is vented, or if desired, recovered for use or sale as a by-product.

After further purification of ethylene oxide, high purity ethylene oxide (HPEO) can be chilled, stored and transported to customers.

Alternatively or additionally, ethylene oxide is often produced in a combined ethylene oxide/ethylene glycol process, which has the advantages that the ethylene epoxidation process intrinsically produces glycols that require work up, and that the combined ethylene epoxidation and glycol work-up processes provide opportunities for heat integration.

Accordingly, the ethylene oxide produced in the ethylene epoxidation plant may be routed to an ethylene glycol unit comprising an ethylene glycol reactor, wherein ethylene oxide is converted to monoethylene glycol (MEG) and heavier glycols by thermal reaction with an excess of water. Typically, a water/ethylene oxide ratio in the range of 7-14 (wt/wt) is used. By means of a series of (typically three) pre-heaters using low-pressure process steam, direct heat exchange with hot process condensate and high-pressure steam, ethylene glycol reactor temperatures in the range of 150-250° C. are used. Under these conditions reaction rates are fast and no catalyst is required. The ethylene oxide hydrolysis reaction produces an effluent containing mainly water and a glycol product stream comprising about 90 wt % monoethylene glycol (MEG), the remainder being predominantly diethylene glycol (DEG), some triethylene glycol (TEG) and a small amount of higher homologues.

The aqueous ethylene glycol reactor effluent is passed through successive ("multiple effect") evaporator columns to remove water, which is returned to the ethylene glycol reactor. Further dehydration of the evaporator effluent then ensues through vacuum distillation to produce a dehydrated ethylene glycol stream, followed by removal of impurities to provide a purified ethylene glycol product stream.

The conventional ethylene glycol recovery line-up consists of typically three to six forward feed multiple effect evaporators operating at decreasing pressures. Heat to the first evaporator is provided through high pressure steam, and the overhead vapor from each evaporator is used in the reboiler of the subsequent evaporator. The effluent of the last evaporator in line generally contains between 20 and 40 wt % water, and is subjected to dehydration in a single distillation column ("glycol dehydrator") under vacuum to provide a dehydrated ethylene glycol stream. Advantageously, the vaporous overhead from the last evaporator (generally at 3 to 8 barg) is at least partially utilized as process steam for various steam consumers in the ethylene oxide/ethylene glycol plant. The collected process condensates from the reboilers of the second, third etc. evaporators are flashed and the hot condensate is used for direct heat exchange in one of the pre-heaters of the ethylene glycol reactor, and further flashed in a water surge drum to produce low-pressure (typically about 3 barg) steam.

There is an ongoing need in the field of ethylene glycol manufacturing for improving the energy efficiency of the ethylene oxide and an ethylene glycol process steps.

Accordingly, the present inventors have sought to provide an improved process for the manufacturing of ethylene glycol, in particular an integrated ethylene oxide/ethylene glycol process that requires less external steam import.

SUMMARY OF THE INVENTION

Figure 1:
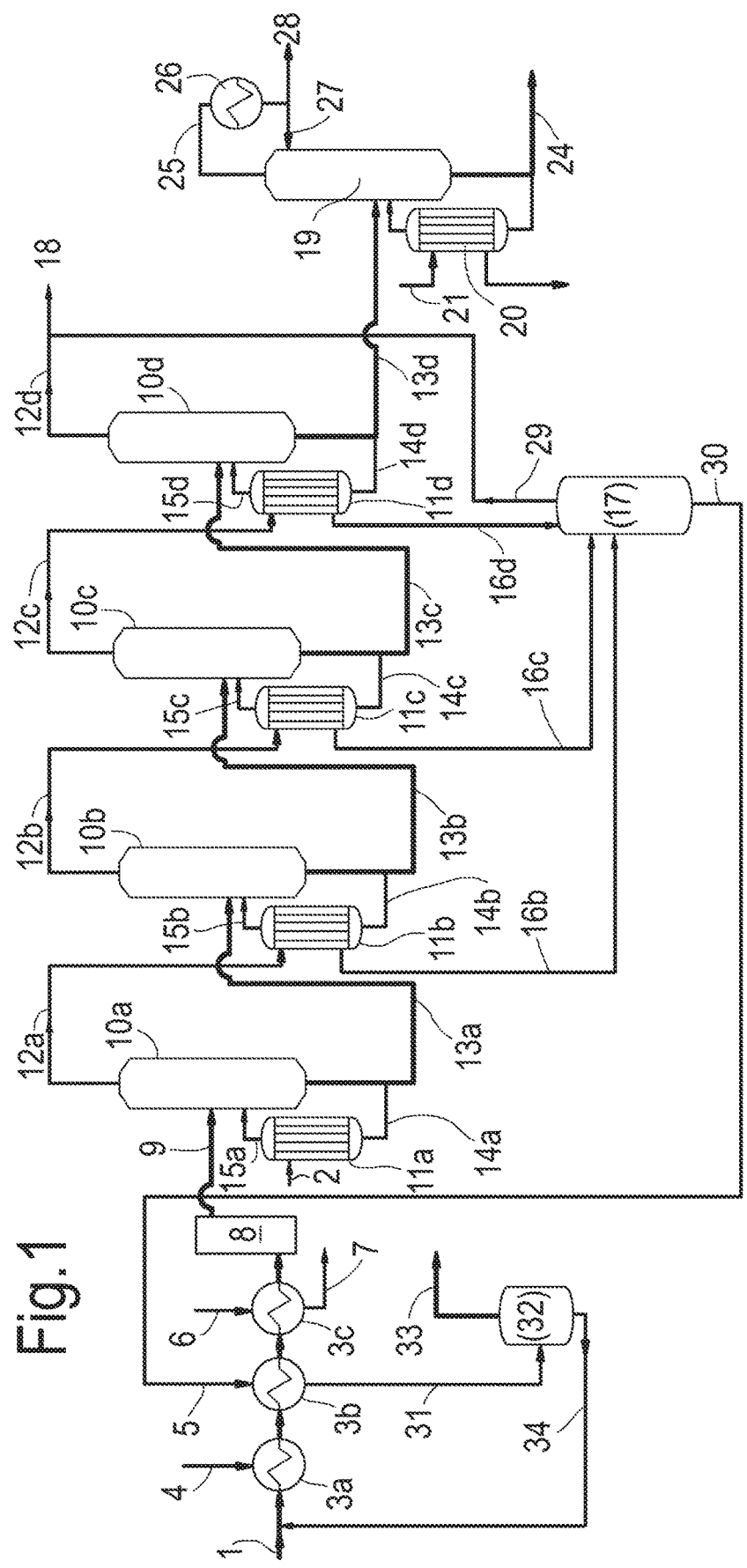
FIG. 1 is a schematic diagram showing a process according to the prior art.

The present inventors have found that in an integrated ethylene oxide/ethylene glycol process, substantial energy savings can be obtained by a process involving a two-step glycol dehydration operation, wherein the effluent of the multiple effect evaporators is subjected to a pre-dehydration step in a distillation column at low (non-vacuum) overhead pressure prior to the conventional ethylene glycol vacuum distillation step.

Thus, in one aspect of the present invention there is provided a process for the recovery of ethylene glycol from an aqueous stream comprising ethylene glycol, said process comprising
(a) subjecting said aqueous stream comprising ethylene glycol to an evaporation step in a multiple-effect evaporator to obtain a concentrated stream comprising ethylene glycol;
(b) subjecting said concentrated stream comprising ethylene glycol to a first dehydration step in a first dehydrator operating at an overhead pressure in the range of 0 barg to 4 barg to obtain a partially dehydrated ethylene glycol stream,
(c) subjecting said partially dehydrated ethylene glycol stream to a second dehydration step in a second dehydrator operating under vacuum to obtain a dehydrated ethylene glycol stream.

As compared to a conventional single vacuum distillation step, the two-step glycol dehydration process as defined in steps (b) and (c), wherein following multi-effect evaporation the glycol is pre-dehydrated in a dehydrator operating at non-vacuum pressure to produce low-pressure overhead steam, allows recovering thermal energy that would otherwise be discarded as low-quality heat (e.g. cooling water).

More specifically, it was found that the overhead vapors of the first dehydrator operating at elevated pressure can effectively be utilized for driving a wide range of low-pressure steam consumers in associated process steps. For example, it was found that two-step glycol dehydration as disclosed herein can be integrated in ethylene oxide/ethylene glycol process such that low-pressure steam generated from the first dehydrator is sufficient to furnish all the chilling requirement of the process, resulting in less or no import of external steam to the process for chilling purposes. Thus, the two-step dehydration of glycols according to the present invention results in increased energy efficiency and reduced process costs of an integrated ethylene oxide/ethylene glycol process.

DETAILED DESCRIPTION OF THE INVENTION

The following definitions apply. First of all, "barg" means "bar gauge". Further, unless indicated otherwise, by pressure reference is made to absolute pressure. The latter implies that a "pressure of 250 mbar" means an "absolute pressure of 250 mbar" (i.e. 250 mbara). Further, "operating under vacuum" means "operating under subatmospheric pressure". Further, gauge pressure equals absolute pressure minus atmospheric pressure. Thus, in a case where the gauge pressure is 0 barg the absolute pressure equals atmospheric pressure.

As mentioned above, the ethylene glycol recovery process according to the present invention is particularly suitable for implementation in an integrated ethylene oxide/ethylene glycol process, by utilizing low-pressure steam produced by the first dehydrator in the back-end ethylene glycol section for driving low-pressure steam consumers in the process.

In the ethylene oxide (EO) process, chilled water is used for cooling of the lean absorbent used in the ethylene oxide absorber, condensing EO stripper overhead vapors and in the EO purification column. Chilled water is typically generated via vapor absorption equipment in which the energy source is either low pressure steam or hot water available from the process. In a conventional ethylene oxide/ethylene glycol process, heat to the chilling equipment is mainly supplied by low pressure steam generated in the monoethylene glycol (MEG) purification column condenser, by condensing EO stripper overhead vapors and/or by the hot lean absorbent from the EO stripper. The conventional ethylene glycol back end process is generally designed with three to six glycol evaporators in line, wherein the last evaporator is typically operated at a pressure of about 5 barg, and wherein its overhead vapor is used as process steam by various steam users in the plant such as the EO stripper reboiler, glycol dehydrator, and $CO_2$ removal stripper reboiler.

In the ethylene glycol recovery process according to the present invention, process steam produced in the last glycol evaporator and/or clean imported steam is used to drive the reboiler of the new first glycol dehydrator ("pre-dehydrator") operating at an overhead pressure in the range of 0 barg to 4 barg in order to produce a partially dehydrated ethylene glycol stream, which is subsequently further dehydrated under vacuum distillation conditions in a second (conventional) dehydrator to produce a dehydrated ethylene glycol stream. Typically, the second (conventional) dehydration step is carried out at a pressure in the range of 50 to 250 mbar, preferably in the range of 100-200 mbar.

Advantageously, the low-pressure overhead vapor of said first glycol dehydrator is used to drive a wide range of low-pressure steam consumers in an ethylene oxide manufacturing process. Thus, in one embodiment of the present invention, the aqueous stream comprising ethylene glycol is produced by a process comprising manufacturing of ethylene oxide and hydrolysis of ethylene oxide, wherein at least a portion of the steam produced in the first dehydrator is used to drive one or more low-pressure steam consumers in the ethylene oxide/ethylene glycol manufacturing process. In one embodiment, the low-pressure steam consumers are one or more chilling units.

As mentioned above, the process of the present invention involves subjecting an aqueous stream comprising ethylene glycol to evaporation in a multiple-effect evaporator line-up. As used herein, the term "multi(ple)-effect evaporator" should be understood to be synonymous to "multi(ple)-stage evaporator", and to refer to an apparatus wherein water is evaporated in a sequence of two or more vessels ("stages"), wherein each evaporator vessel is held at a lower pressure than the preceding vessel, and wherein the vapor boiled off in one vessel is used to heat the reboiler of the next vessel in line. Herein, only the first vessel (at the highest pressure) requires an external source of heat. The use of multiple-effect evaporation for the recovery of ethylene glycol, in particularly in integrated ethylene oxide/ethylene glycol manufacturing has been described in detail in the prior art, notably in U.S. Pat. Nos. 3,875,019, 6,417,411, Ullmann's Encyclopedia of Industrial Chemistry, seventh edition. In the process of the present invention, the multiple-effect evaporation step may be carried out in the conventional manner, and the skilled person will be able to select appropriate conditions depending on the desired degree of water removal. Typically, the multiple-effect evaporation step is performed in 2 to 6 stages (evaporator vessels) or 3 to 6 stages, preferably 2 to 5 stages, more preferably 3 or 4 stages. Preferably, the heat duty of the first evaporator vessel in line is adjusted such that the water content in the feed to the second dehydrator is similar to that of the conventional process using only a single dehydrator operating under vacuum. Preferably, heat to the first evaporator vessel is provided by high pressure steam having a pressure in the range of 20 to 30 barg, more preferably in the range of 22 to 28 barg, most preferably in the range of 24 to 26 barg.

Typically, the vaporous overhead from the last evaporator vessel in the multiple-effect evaporator line-up is used as process steam, preferably at a pressure in the range of 3 to 8 barg, more preferably in the range of 4 to 6 barg, most preferably in the range of 4.5 to 5.5 barg. Advantageously, at least a portion of the vaporous overhead from the last evaporator vessel may be used to provide heat to the first dehydrator by driving the reboiler of the first dehydrator. According to the present disclosure, said first dehydrator is operated at an overhead pressure in the range of 0 barg to 4 barg.

Thus, in one embodiment, the vaporous overhead from the last evaporator vessel in the multiple-effect evaporator is used as process steam, wherein at least a portion of said process steam is used to provide heat to the first dehydrator.

The first dehydrator is preferably operated at an overhead pressure in the range of 0.3-3 barg, more preferably in the range of 0.5-1.5 barg, most preferably in the range of 0.8 barg to 1.2 barg.

Advantageously, the reboiler duty of the first dehydrator is chosen such that its overhead vapor provides sufficient process steam to cater for all the low-pressure steam requirement, such as chilling apparatuses, of the ethylene oxide/ethylene glycol process. Preferably, the bottom temperature of the first dehydrator is lower than 150° C., preferably lower than 145° C. in order to provide sufficient logarithmic mean temperature difference (LMTD) for using the overhead of the last evaporator as process steam in its reboiler.

The first dehydrator may be any suitable sort of column known in the art and may be equipped with trays or packing equivalent to theoretical stages between 2 and 10. The number of (theoretical) trays may vary in the range of from 2 to 10 and may easily be determined by the skilled person on the basis of simple economic optimization experiments.

As described above, an ethylene glycol section generally comprises a monoethylene glycol (MEG) purification column, said MEG purification column being equipped with an overhead condenser wherein vapors from the overhead of the MEG purification column are condensed to produce low-pressure steam and condensate, which is partially retuned to the MEG purification column as reflux.

In one embodiment, the improved ethylene glycol section of the present invention is integrated with an improved ethylene oxide section comprising an ethylene oxide (EO) stripper, wherein said ethylene oxide stripper contains a first and an additional, second reboiler, and wherein heat is supplied to said second ethylene oxide stripper reboiler by low-pressure steam generated in the monoethylene glycol (MEG) purification column overhead condenser. Typically, the MEG column condenser produces steam having a pressure in the range of 1 to 4 barg, preferably in the range of 1.5 to 3 barg, more preferably in the range of 2 to 2.5 barg. While, as described above, in a conventional ethylene oxide/ethylene glycol process, heat to drive front-end chilling equipment is mainly supplied by low pressure steam from the monoethylene glycol (MEG) overhead column condenser, the present use of low-pressure steam from the first (pre-)dehydrator overhead to drive such chilling equipment allows for utilizing the low-pressure steam from the MEG overhead column condenser in said additional side reboiler of the EO stripper. Preferably, the second side reboiler duty is fixed and set equal to or a bit lower than the MEG column condenser duty such that all the low-pressure steam produced in the MEG condenser is consumed in the side reboiler and excess steam vent from the plant is minimized.

Advantageously, this reduces duty of the first, (knockback section) reboiler of the EO stripper which conventionally relies on higher-pressure steam import, thus reducing the total steam consumption for the integrated ethylene oxide/ethylene glycol process.

Additionally, a cold "external" reflux of fat absorbent may be added in the top of the EO Stripper column, as described in detail in WO 2006/120207, the contents of which are incorporated by reference herein. The unheated, fat absorbent stream, preferably from an EO absorber bottom or from a residual EO absorber bottom, enters the EO stripper at least one stage above the hot, flashing fat absorbent stream. Energy is transferred from the ethylene oxide and water vapor leaving the stripping section to the unheated fat absorbent stream within an additional rectifying section. This is an improvement with respect to the traditional reflux of the EO stripper where a portion of the EO stripper overhead is condensed and recycled back to the column. Due to the reduced use of steam directly introduced at the bottom of the EO stripper, this also results in energy savings.

Thus, in one embodiment, the improved ethylene glycol section of the present invention is integrated with an improved ethylene oxide section comprising an ethylene oxide stripper to which fat absorbent is supplied at elevated temperature, and wherein one or more external process stream feeds are provided to the EO stripper at a location above the elevated temperature fat absorbent feed and at a lower temperature with respect to the elevated temperature fat absorbent feed. In one embodiment, at least a portion of the fat absorbent stream from the ethylene oxide absorber bottom is used as the external process stream feed provided at lower temperature to the EO stripper. In a preferred embodiment, the ethylene oxide section comprises a residual ethylene oxide absorber, wherein at least a portion of the fat absorbent stream from the residual absorber bottom is used as the external process stream feed provided at lower temperature to the EO stripper.

Advantageously, the residual EO absorber may be supplied with fat absorbent from the EO absorber bottom in its lower section (i.e., above the point where light ends and uncondensed ethylene oxide are fed), resulting in a substantial reduction in its lean absorbent requirement, which in turn reduces recycling of the water circulation, thus saving stripping steam in the EO stripper and lean absorbent chilling. Typically, a packed bed equivalent to one to five theoretical stages would be provided in the lower section of the residual EO absorber in order to optimize the lean absorbent flow. Accordingly, in one embodiment, the ethylene oxide section comprises a residual ethylene oxide absorber, wherein at least a portion of the fat absorbent stream from an ethylene oxide absorber bottom is provided above the point where a feed comprising ethylene oxide is provided to said residual ethylene oxide absorber.

Reduction in the lean absorbent flow to the residual EO absorber reduces recycling of the water circulation, which saves stripping steam in the EO stripper and lean absorbent chilling.

In prior art ethylene oxide/ethylene glycol processes, condensates from the second, third etc., reboilers of the multiple-effect evaporator are typically collected in a process condensate drum operating at 5-15 barg and flashed to provide about 3 to 7 barg process steam, which is used in the process as open steam in a carbon dioxide stripper and in vacuum ejectors, whereas the condensate is used for heat exchange in a pre-heater of the ethylene glycol reactor, further flashed in a water surge drum to provide lower pressure steam, and the condensate from the water surge drum is supplied as recycle process condensate to the ethylene glycol reactor.

In the present invention, advantageously, the process condensate drum for condensates from the second, third etc. reboilers of the multiple-effect evaporator is operated at a reduced pressure in the range of 4-10 barg. The collected condensates of the multiple-effect evaporator are flashed to produce flash steam with a pressure in the range of 3 to 7 barg, wherein the condensate from the process condensate drum is directly recycled to the ethylene glycol reactor. Thus, in one embodiment, the collected condensates of the multiple-effect evaporator are flashed to produce flash steam and flash condensate, wherein at least a portion of the flash condensate is recycled to an ethylene glycol reactor.

In addition to the advantages mentioned above for heat integration in an ethylene oxide/ethylene glycol process and associated equipment, the direct recycle of condensate from the process condensate drum to the glycol reactor rather than through heat exchange allows for the use of a single ethylene glycol reactor pre-heater, operating at high-pressure steam.

In the process of the invention, steam produced in the first dehydrator is advantageously used to drive one or more low-pressure steam consumers in the process. The process condensate from these low-pressure steam consumers may be recycled to a low-pressure water surge drum, and at least a portion thereof may be used to provide reflux of the first dehydrator. Accordingly, in one embodiment, at least a portion of the condensate of the one or more low-pressure steam consumers in the ethylene oxide section is used to supply reflux to the first dehydrator.

The ethylene glycol process produces aldehydes as a by-product. In the conventional line-up, aldehydes in the system are typically bled from the ethylene glycol evaporators via process condensate bleed from the water surge drum to waste water, through routing of condensate of the 3 barg steam from the water surge drum to waste water, and through use of the 3-7 barg process steam (flashed from process condensate drum) as open steam in a carbon dioxide stripper and in vacuum ejectors In process of the present invention, there is no bleed from the water surge drum 3 barg overhead vapor. Hence, in the present process care should be taken to bleed sufficient 5 barg process steam from the system via use as open steam to the $CO_2$ stripper and use in the vacuum ejectors to purge out aldehydes from the system. Preferably, provisions are also made to bleed aldehydes via condensate bleed from both the process condensate drum and the water surge drum to waste water if required.

After obtaining dehydrated ethylene glycol stream from the second dehydrator, monoethylene glycol (MEG) and optionally diethylene glycol (DEG) and triethylene glycol (TEG) may be recovered from the dehydrated ethylene glycol stream by fractional distillation methods known in the art. As mentioned above, low-pressure steam generated in the MEG column overhead condenser may be utilized in driving a second side reboiler of the ethylene oxide stripper.

DETAILED DESCRIPTION OF THE DRAWINGS

The invention will now be described in detail with reference to the non-limiting embodiments shown in the Figures.

FIG. 1 shows a schematic drawing of an ethylene glycol unit according to the prior art, comprising an ethylene glycol reactor, evaporators and a (vacuum) dehydrator. An aqueous ethylene oxide feed stream (1) is supplied to a first (3a), second (3b) and third (3c) ethylene glycol reactor pre-heater, to which heat is supplied in the form of low-pressure steam (4), direct heat exchange with hot process condensate (5) and high-pressure steam (6), respectively, to ethylene glycol reactor and associated equipment (8). Herein, the aqueous ethylene oxide stream is converted to an aqueous ethylene glycol stream (9), which is supplied to the first evaporator (10a) (first stage) of a multiple-effect evaporator further comprising (as an example) a second (10b), third (10c) and fourth (10d) evaporator (second, third and fourth stages), each next evaporator in line operating at lower pressure than the previous evaporator. Heat to the first evaporator (10a) is provided through high pressure steam stream (2). Each stage of the multiple-effect evaporator comprises a reboiler (11a), (11b), (11c) and (11d), producing vapor/liquid-containing reboiler return streams (15a), (15b), (15c), and (15d), respectively, providing heat to the bottom of each evaporator. The vaporous overheads (12a), (12b) and (12c) of each evaporator are supplied to the reboiler (11b), (11c) and (11d) of the next evaporator in line, respectively. Each evaporator produces an increasingly concentrated stream (13a), (13b), (13c), and (13d) which is supplied as feed stream to the next evaporator (10b), (10c) and (10d) in line, respectively. The concentrated glycol streams (14a), (14b), (14c) and (14d) of the evaporators are recycled to reboilers (11a), (11b), (11c) and (11d), respectively. The vaporous overhead (12d) of the last evaporator in line (generally at 3 to 8 barg) is generally at least partially utilized as process steam for various steam consumers in the ethylene oxide/ethylene glycol plant. The process condensates (16b), (16c) and (16d) from the reboilers of the second, third, and fourth evaporators are collected in process condensate flash drum (17) and flashed to provide ~3-7 barg process steam (29). Hot condensate stream (30) is used for direct heat exchange, as stream (5), in pre-heater (3b) of the ethylene glycol reactor, and cooled stream (31) is flashed in water surge drum (32) to produce lower-pressure steam stream (33). Condensate stream (34) is recycled to the ethylene glycol reactor by providing it upstream of the first pre-heater (3a). Concentrated ethylene glycol stream (13d) is provided to glycol dehydrator (19) equipped with a reboiler (20) having steam inlet (21), and operating under vacuum to produce a dehydrated glycol stream (24). The vaporous dehydrator overhead stream (25) is partially recycled to the dehydrator and a portion may be removed as waste water stream (28).

Figure 2:
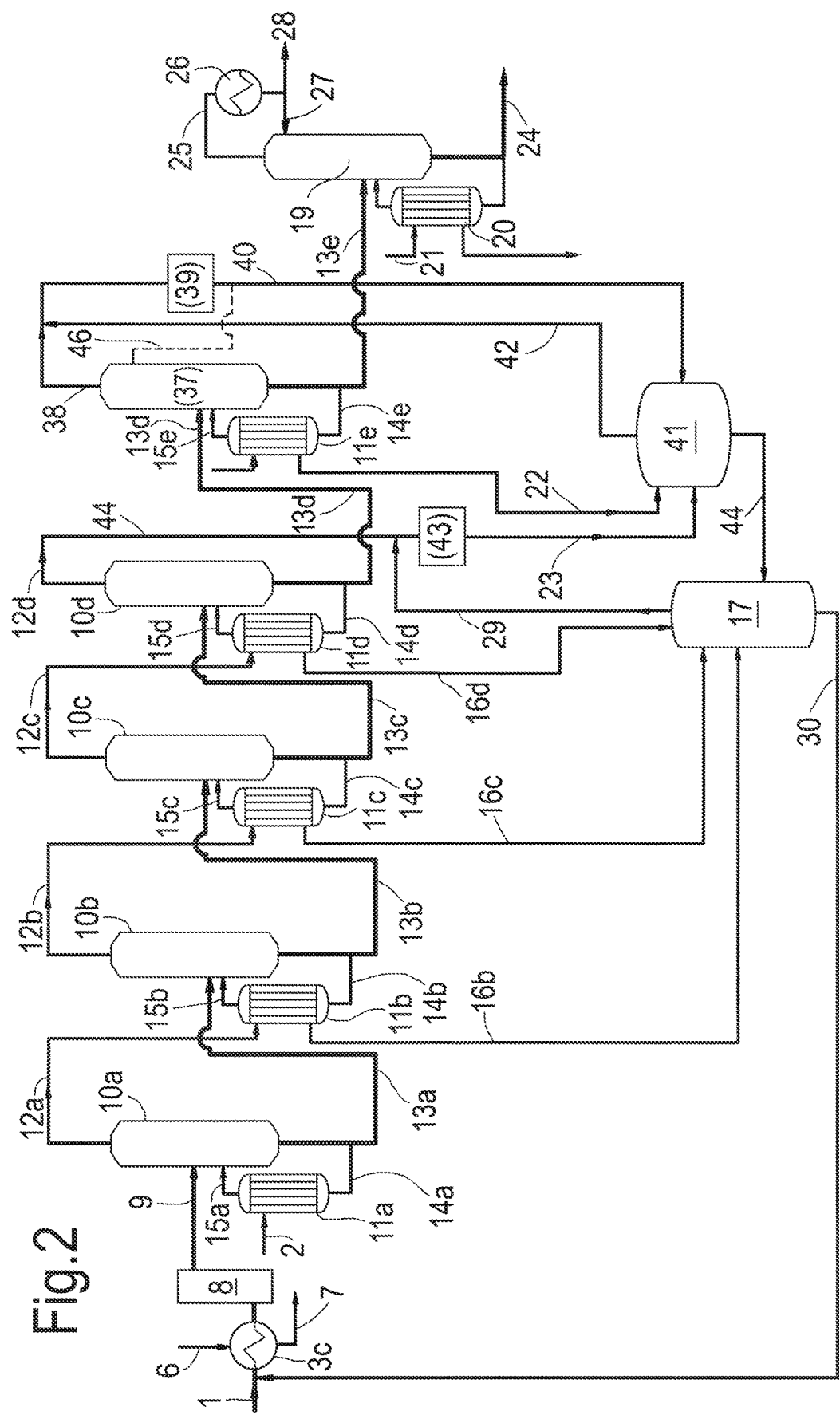
FIG. 2 is a schematic diagram showing a process according to an embodiment of the invention.

FIG. 2 shows a schematic drawing of an ethylene glycol unit according to the present invention. An aqueous ethylene oxide feed stream (1) is supplied to a single ethylene glycol reactor pre-heater (3c), to which heat is supplied in the form of high-pressure steam (6), and the pre-heated ethylene oxide is stream subsequently supplied to ethylene glycol reactor and associated equipment (8), to produce aqueous ethylene glycol stream (9). Aqueous ethylene glycol stream (9) is supplied to the first evaporator (10a) (first stage) of a multiple-effect evaporator further comprising (as an example) a second (10b), third (10c) and fourth (10d) evaporator as described in detail for FIG. 1. In the process and system according to the present invention, the concentrated ethylene glycol stream (13d) leaving the last evaporator of the multiple-effect evaporator is provided to a first dehydrator (37) operating at an overhead pressure in the range of 0 barg to 4 barg to produce a partially dehydrated ethylene glycol stream (13e) which is provided to a second dehydrator (19) operating under vacuum as described for FIG. 1, to obtain a dehydrated ethylene glycol stream (24). The vaporous overhead stream (38) of first dehydrator (37), having a pressure in the range of 0 barg to 4 barg is utilized by low-pressure steam consumers elsewhere in the process, such as chilling unit (39). Low-pressure condensate streams (40), (22) and/or (23) are collected in water surge drum (41) and flashed to produce low pressure steam (42) that can be utilized by low-pressure steam consumers in the process. Process condensate (40) from low pressure steam user (39) may also be used to supply reflux, via line (46), to first glycol dehydrator (37).

Process condensates (16*b*), (16*c*) and (16*d*) from the reboilers of the second, third, and fourth evaporators, and condensate (44) from water surge drum (41) are collected in process condensate flash drum (17) and flashed to provide process steam (29) suitable for use by ~3-6 barg steam consumers (43) in the process. Advantageously, at least a portion of the vaporous overhead (12*d*) from the last evaporator vessel (10*d*) is used to provide heat to the dehydrator (37) by driving the reboiler (11*e*) of the first dehydrator (37). Hot condensate stream (30) is recycled to ethylene glycol reactor (8) by directly providing it upstream of ethylene glycol reactor pre-heater (3*c*).

Figure 3:
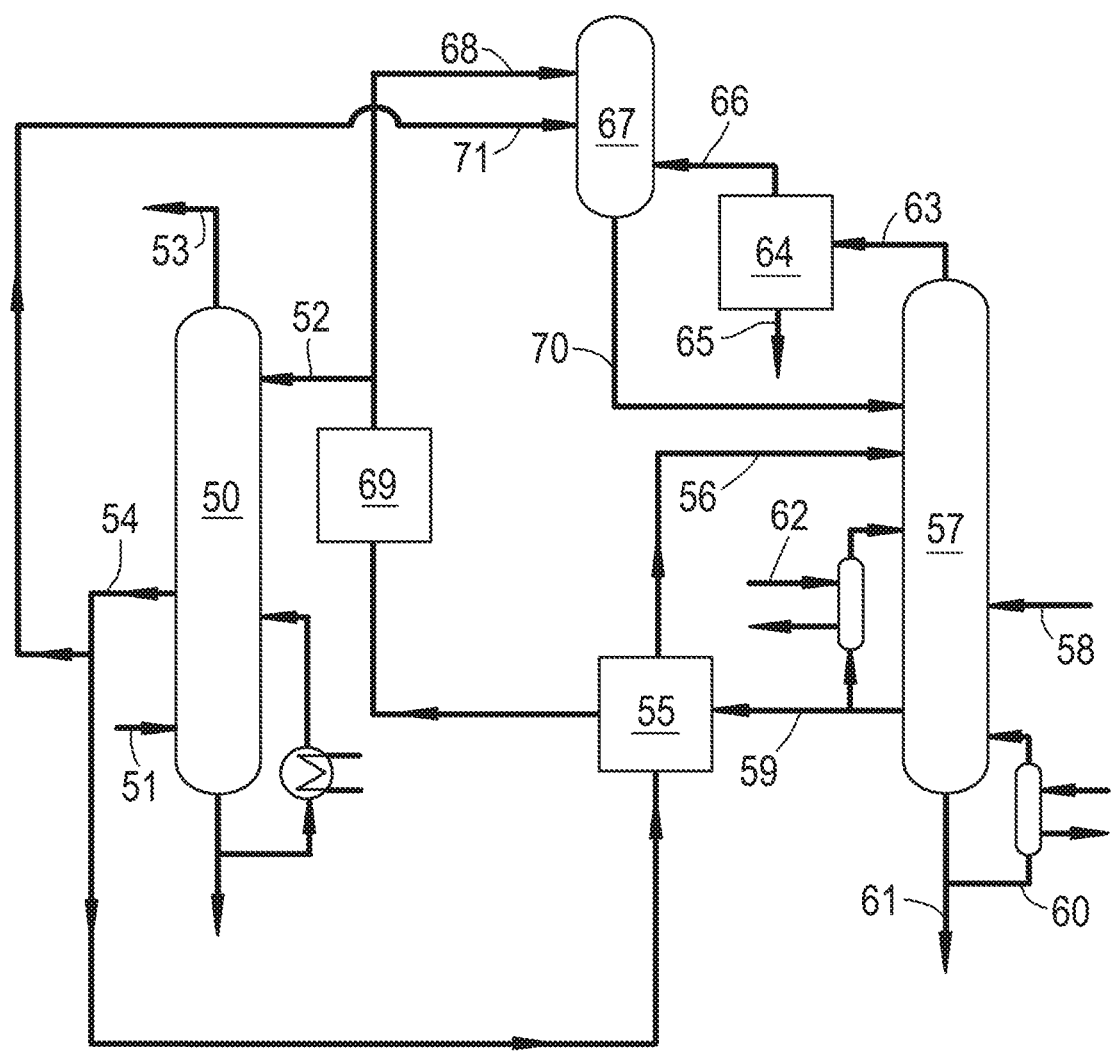
FIG. 3 is a schematic diagram showing a process according to an embodiment of the invention.

FIG. 3 shows a schematic drawing of an ethylene oxide recovery section according to an embodiment of the present invention. An ethylene oxide-containing stream (51) is provided to ethylene oxide absorber (50) to which a cooled lean absorbent stream (52) is supplied, to provide an overhead stream (53) and a fat absorbent stream (54). Fat absorbent stream (54) is contacted in one or more heat exchangers (55) with a hot lean absorbent stream (59) to provide hot fat absorbent stream (56), which is provided to ethylene oxide stripper (57). In ethylene oxide stripper (57), using steam provided through inlet (58), ethylene oxide is stripped from the fat absorbent to provide a lean absorbent stream (59) and an overhead stream (63) comprising ethylene oxide and water. A glycol bleed steam is removed via outlet (61). According to a preferred embodiment of the present invention, ethylene oxide stripper (57) comprises, in addition to a first reboiler (60), a second reboiler (62) operating on low-pressure steam produced elsewhere in the plant, such as in an monoethylene glycol overhead condenser, thus reducing duty of bottom reboiler (60). Ethylene oxide stripper overhead stream (63) is provided to one or more condenser units (64) to provide aqueous ethylene oxide stream (65) and a vapour stream (66) comprising light ends and uncondensed ethylene oxide. Uncondensed ethylene oxide is recovered from the light ends in residual ethylene oxide absorber (67), to which a cold lean absorbent stream (68) is provided. This cold lean absorbent stream (68) is obtained through heat exchange of hot lean absorbent stream (59) with cold fat absorbent stream (54) in one or more heat exchangers (55), and cooling in one or more cooling/chilling units (69).

According to a preferred embodiment of the present invention, a cold fat absorbent stream (70) withdrawn from residual ethylene oxide absorber (67) is provided to ethylene oxide stripper (57) at a point above the hot fat absorbent stream (56), thus providing external reflux to the stripper column. In this embodiment, at least a portion (71) of the cold fat absorbent stream (54) withdrawn from the bottoms of ethylene oxide absorber (50) is provided to residual ethylene oxide absorber (67) above the point where the feed (66) comprising ethylene oxide is provided to residual ethylene oxide absorber (67), thus reducing the lean absorbent requirement (provided through stream (68)) of residual absorber (67).

That which is claimed is:

1. A process for the recovery of ethylene glycol from an aqueous stream comprising ethylene glycol, said process comprising (a) subjecting said aqueous stream comprising ethylene glycol to an evaporation step in a multiple-effect evaporator to obtain a concentrated stream comprising ethylene glycol and a stream of collected condensates;
(b) subjecting said concentrated stream comprising ethylene glycol to a first dehydration step in a first dehydrator operating at an overhead pressure in the range of 0 barg (bar gauge) to 4 barg (bar gauge) to obtain a partially dehydrated ethylene glycol stream and a low pressure steam stream at a pressure in the range of 0 barg to 4 barg, and
(c) subjecting said partially dehydrated ethylene glycol stream to a second dehydration step in a second dehydrator operating under vacuum to obtain a dehydrated ethylene glycol stream, wherein the collected condensates of the multiple-effect evaporator are flashed to produce flash steam and flash condensate, and wherein at least a portion of the flash condensate is recycled to an ethylene glycol reactor.

2. The process according to claim 1, wherein said aqueous stream comprising ethylene glycol is produced by a process comprising manufacturing of ethylene oxide in an ethylene oxide section and hydrolysis of ethylene oxide in an ethylene glycol section, and wherein the ethylene oxide section or the ethylene glycol section comprise one or more low-pressure steam consumers and using at least a portion of the low pressure steam produced in the first dehydrator to drive the one or more low-pressure steam consumers in the ethylene oxide section or the ethylene glycol section.

3. The process according to claim 2, wherein said low-pressure steam consumers comprise one or more chilling units.

4. The process according to claim 1, wherein the multiple-effect evaporation step is performed in 2 to 6 stages.

5. The process according to claim 1, wherein the first dehydrator is operated at a pressure in the range of 0.3-3 barg.

6. The process according to claim 1, wherein the vaporous overhead from the last evaporator vessel in the multiple-effect evaporator is used as process steam, and wherein at least a portion of said process steam is used to provide heat to the first dehydrator.

7. The process according to claim 2, wherein at least a portion of the condensate of the one or more low-pressure steam consumers is used to supply reflux to the first dehydrator.

8. The process according to claim 2, wherein the ethylene oxide section comprises an ethylene oxide (EO) stripper, wherein said ethylene oxide stripper contains a first and an additional, second reboiler, and wherein heat is supplied to said second ethylene oxide stripper reboiler by low-pressure steam generated in a monoethylene glycol (MEG) purification column overhead condenser.

9. The process according to claim 2, wherein the ethylene oxide section comprises an ethylene oxide stripper to which fat absorbent is supplied, and wherein one or more external process stream feeds are provided to the ethylene oxide stripper at a location above the fat absorbent feed.

10. The process according to claim 9, wherein at least a portion of the fat absorbent stream from an ethylene oxide absorber bottom is used as the external process stream feed.

11. The process according to claim 9, wherein the ethylene oxide section comprises a residual ethylene oxide absorber, wherein at least a portion of the fat absorbent stream from the residual absorber bottom is used as the external process stream feed.

12. The process according to claim 2, wherein the ethylene oxide section comprises a residual ethylene oxide absorber, wherein at least a portion of the fat absorbent stream from an ethylene oxide absorber bottom is provided above the point where a feed comprising ethylene oxide is provided to said residual ethylene oxide absorber.

\* \* \* \* \*